(12) United States Patent
Hautiere et al.

(10) Patent No.: US 7,873,188 B2
(45) Date of Patent: Jan. 18, 2011

(54) DEVICE FOR MEASURING VISIBILITY DISTANCE

(75) Inventors: Nicolas Hautiere, Paris (FR); Raphaël Labayrade, Versailles (FR); Didier Aubert, Mennecy (FR)

(73) Assignees: Laboratoire Central des Ponts et Chaussees, Paris (FR); Institut National de Recherche sur les Transports et leur Securité, Arcueil (FR)

( * ) Notice: Subject to any disclaimer, the term of this patent is extended or adjusted under 35 U.S.C. 154(b) by 838 days.

(21) Appl. No.: 11/665,535

(22) PCT Filed: Oct. 19, 2005

(86) PCT No.: PCT/FR2005/050867
§ 371 (c)(1),
(2), (4) Date: Aug. 2, 2007

(87) PCT Pub. No.: WO2006/043003
PCT Pub. Date: Apr. 27, 2006

(65) Prior Publication Data
US 2008/0137911 A1     Jun. 12, 2008

(30) Foreign Application Priority Data
Oct. 19, 2004   (FR) .................. 04 11061

(51) Int. Cl.
*G06K 9/00*    (2006.01)
(52) U.S. Cl. .................. 382/106
(58) Field of Classification Search ............. 382/100, 382/103, 104, 105, 106
See application file for complete search history.

(56) References Cited

U.S. PATENT DOCUMENTS

| | | | |
|---|---|---|---|
| 5,195,144 A * | 3/1993 | Le Parquier et al. | 382/104 |
| 5,987,152 A | 11/1999 | Weisser | |
| 6,208,938 B1 | 3/2001 | Doerfel | |
| 6,362,773 B1 | 3/2002 | Poechmueller | |
| 7,321,669 B2 * | 1/2008 | Southall et al. | 382/106 |
| 2003/0197867 A1 | 10/2003 | Kwon | |
| 2005/0013456 A1 * | 1/2005 | Chalupper et al. | 381/312 |

FOREIGN PATENT DOCUMENTS
FR    2 847 367 A    5/2004

* cited by examiner

*Primary Examiner*—Brian Q Le
(74) *Attorney, Agent, or Firm*—Kenyon & Kenyon LLP

(57) ABSTRACT

The invention relates to a device for determining visibility distance in a landscape. The device comprises a camera for taking an image of said landscape; means for storing said image; means for associating each pixel of the image with information representative of the distance between the camera and the point in the landscape corresponding to said pixel, thereby obtaining a map of distances; means for processing the image to detect whether a pixel of the image presents contrast greater than a predetermined value relative to at least some adjacent pixels; means for applying said processing for detecting contrast successively to the pixels of the image beginning from the pixel corresponding to the greatest distance and continuing to the first pixel found to satisfy the contrast condition; and means for associating said pixel with distance information from said map of distances.

5 Claims, 1 Drawing Sheet

DEVICE FOR MEASURING VISIBILITY DISTANCE

This is a 371 national phase application of PCT/FR2005/050867 filed 19 Oct. 2005, claiming priority to French Patent Application No. FR 0411061 filed 19 Oct. 2004, the contents of which are incorporated herein by reference.

The present invention provides a device for measuring visibility distance, particularly but not exclusively for mounting on a vehicle.

BACKGROUND OF THE INVENTION

The definition generally used for visibility distance, and more particularly for weather visibility distance is as follows: it is the distance beyond which a black object of appropriate size is perceived with contrast that is less than a predetermined value that is of the order of 2% to 5%. Contrast between two objects is commonly defined by Michelson's formula:

$$C = \frac{L_{max} - L_{min}}{L_{max} + L_{min}}$$

In this formula, $L_{max}$ designates the luminance of the lighter object and $L_{min}$ the luminance of the darker object.

Other formulae can be used, for example Weber's contrast:

$$C = \frac{L_{max} - L_{min}}{L_{min}}$$

Calculating visibility distance, and more precisely weather visibility distance, is useful for at least two reasons. Firstly, measuring visibility distance itself can enable the driver of a vehicle to be provided with information enabling driving to be adapted to visibility conditions. Secondly, measuring weather visibility distance does not serve only in a system for detecting objects. More generally, it can be useful in providing driving assistance in any circumstances in which it is necessary to perceive certain components in the surroundings, for example in an application to detecting the road.

Making use of weather visibility distance measurements to provide driving assistance does not only involve adjusting the measurement sensor. Means providing driving assistance based on knowledge about visibility can serve, for example, to warn a driver that operation thereof is degraded, or even that driving assistance is deactivated since conditions lie outside the operating range of said means.

OBJECT AND SUMMARY OF THE INVENTION

An object of the present invention is to provide a device capable of being mounted on board a vehicle and serving, under all visibility situations, to calculate the weather visibility distance for the surroundings of the vehicle.

To achieve this object, according to the invention, the device for determining visibility distance in a landscape comprises:
a camera for taking an image of said landscape in which visibility distance is to be determined;
means for storing said image;
means for associating each pixel of the image with information representative of the distance between the camera and the point in the landscape corresponding to said pixel, thereby obtaining a map of distances;
image processor means for detecting whether a pixel of the image presents contrast greater than a predetermined value relative to at least some adjacent pixels;
means for applying said contrast detection treatment successively to the pixels in the image starting with the pixel corresponding to the greatest distance and continuing to the first pixel found to satisfy the contrast condition; and
means for associating distance information with said pixel from said map of distances, said distance information being the visibility distance.

It will be understood that the device for determining visibility distance comprises a camera for taking an image of the landscape in which it is desired to determine said distance, means for associating each pixel of the image with information representative of the distance between the camera and the point in the landscape corresponding to the pixel, and means for processing this information. The processor means implement an algorithm for measuring contrast by applying Michelson's formula or any other contrast formula, and means for applying the contrast detection treatment to the pixels of the image in succession by scanning the image beginning with the pixel corresponding to the greatest distance from the camera and continuing until a pixel is detected that is found to present contrast greater than the predetermined value. The distance between the camera and the point in the landscape corresponding to the first pixel that presents the predetermined contrast provides the visibility distance, and more precisely the weather visibility distance.

In a first embodiment of the invention, the means for associating each pixel of the image with information representative of distance comprise a second camera for taking images. The information representative of distance is then extracted by known means for processing the stereovision image that is thus obtained using two cameras.

In a second embodiment, the means for associating each pixel of the image with information representative of distance comprise a telemeter device for scanning the landscape in front of the camera. It is thus possible to associate each pixel of the image with information representative of distance relative to the camera as provided by the telemeter device.

BRIEF DESCRIPTION OF THE DRAWING

Other characteristics and advantages of the invention appear better on reading the following description of a plurality of embodiments given as non-limiting examples.

MORE DETAILED DESCRIPTION

Figure 1:
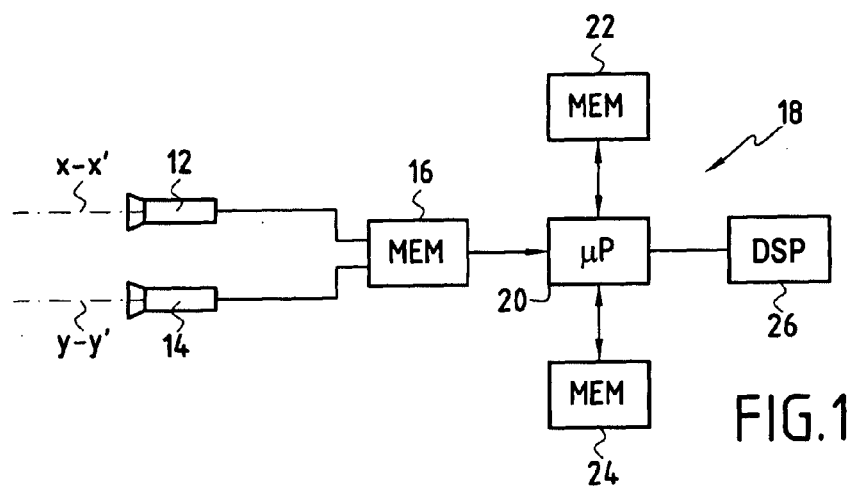
FIG. 1 is a simplified view of a first embodiment of a device for measuring visibility distance.

With reference initially to FIG. 1, a first embodiment of the device for measuring visibility distance is described for the situation in which the device is mounted on a vehicle. Two cameras 12 and 14 are shown mounted at the front of the vehicle, having axes x-x' and y-y' that are pointed in such a manner as to ensure that the two cameras 12 and 14 together provide a stereovision image of the landscape in front of the vehicle. Usually, the landscape contains the road on which the vehicle is traveling. Preferably, the cameras 12 and 14 are digital cameras and thus deliver information relating to the various pixels of the image directly in digital form. It would also be possible to use analog cameras in association with analog-to-digital converters. The digital information corresponding to the images taken by the cameras 12 and 14 respectively are stored in a memory 16.

The information relating to these two images is processed by a processor assembly 18 constituted essentially by a microprocessor 20, a program memory 22, and a data memory 24. The program memory 22 contains firstly a program Prog 1 for generating a map of differences from the pixel information of the two images stored in the memory 16. The memory 22 also contains a second program Prog 2 for calculating contrast between a pixel of an image and the surrounding pixels, e.g. by implementing Michelson's formula. The memory 22 contains a third program Prog 3 for scanning the pixels of the image of the landscape so as to calculate the contrast of each pixel in succession by using the program Prog 2. Finally, a program, Prog 4, for determining visibility distance serves, once a pixel of desired contrast has been detected, to calculate the actual distance between the position of the camera and the point of the landscape associated with that pixel so as to obtain thereby the visibility distance. Finally, the measurement device advantageously includes a display system 26 for displaying the previously calculated visibility distance.

There follows an explanation of the various steps in the processing that enables the visibility distance to be obtained. Using the program Prog 1, the microprocessor 20 establishes a map of differences on the basis of the digital information corresponding to the two images taken respectively by the cameras 12 and 14. This map of differences thus contains information representative of the different positions in the images taken by the two cameras of a common point in the landscape. The way in which the map of differences is generated is described in "In-vehicle obstacles detection and characterization by stereovision", by Raphael Labayrade and Didier Aubert, In Vehicle Cognitive Computer Vision Systems, ICVS, Gratz, Apr. 3, 2003.

The map of differences is stored in the data memory 24 and constitutes a map of distances. Naturally, it is necessary to perform initial calibration on the measurement installation. On the basis of the map of differences, the scanner program Prog 3 scans the pixels of the image successively, beginning with the pixels corresponding to the greatest distance from the camera. For each pixel, the program Prog 2 for calculating contrast is run. The program Prog 2 implements the algorithm corresponding to Michelson's formula as defined above, or any other selected formula for measuring contrast. In order to calculate contrast from such formulae, it is possible to use Köhler's method as described in the article by R. Köhler "A segmentation technique based on thresholding", CVGIP 15, 1981, pages 319-338. Once a pixel is associated with contrast greater than a predetermined value, which in the example under consideration is 5%, the program Prog 4 interrupts scanning and uses the information contained in the various maps stored in the memory 24 to calculate the actual distance between the camera and the point in the landscape corresponding to the image pixel having the required contrast. By way of example, this distance is displayed on the display device 26. Naturally, calculating the actual distance requires initial calibration of the information delivered by the cameras.

When the device is mounted on a self-propelled vehicle, the visibility distance information is naturally calculated at predetermined intervals and can serve to provide automatic control over some of the functions of the vehicle. For example, the information may serve to limit speed or to monitor distance from a vehicle in front of the vehicle fitted with the measurement device when said vehicle is fitted with means for measuring distances relative to another vehicle.

As mentioned above, this visibility distance value can also be used for controlling a device that measures distances to obstacles that is also fitted to the vehicle.

Figure 2:
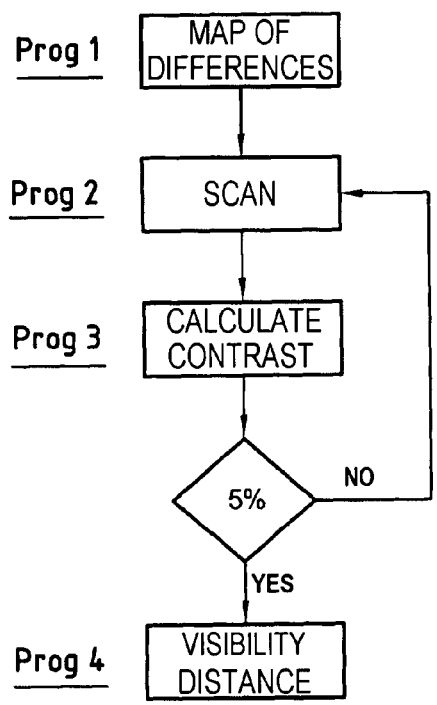
FIG. 2 is a flow chart of the processing method implemented by the device.
Figure 3:
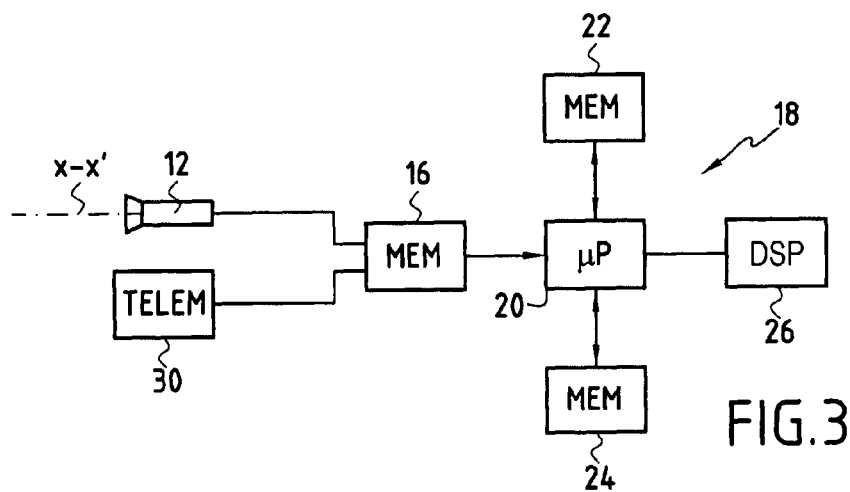
FIG. 3 is a simplified view of a second embodiment of the device for measuring visibility distance.

In a second embodiment of the invention, the only difference from the first embodiment consists in the definition of the means for associating each pixel of the image with information representative of the distance between the camera taking the images and the point in the landscape associated with a pixel. More precisely, in the second embodiment, the stereovision image is replaced by a single image, and distance information is provided by a telemeter device 30 which scans the landscape whose image is taken by the camera 12. The memory associated with the processor means thus receives firstly digital information corresponding to the various pixels of the image as taken, and secondly distance information as delivered by the telemeter device, thereby constituting a distance map. Naturally, the camera and the telemeter device need to be subjected to initial calibration. On the basis of this information, the treatment performed by the microprocessor 20 is the same as that described above with reference to FIGS. 1 and 2.

More precisely, the difference map is replaced by the set of distances delivered by the telemeter means, and the scanning of the image as a function of distance is controlled on the basis of the distance information delivered by the telemeter device itself.

What is claimed is:

1. A device for determining visibility distance in a landscape, the device comprising:
   a camera for taking an image of said landscape in which visibility distance is to be determined;
   means for storing said image;
   means for associating each pixel of the image with information representative of the distance between the camera and the point in the landscape corresponding to said pixel, thereby obtaining a map of distances;
   image processor means for detecting whether a pixel of the image presents contrast greater than a predetermined value relative to at least some adjacent pixels;
   means for applying said contrast detection treatment successively to the pixels in the image starting with the pixel corresponding to the greatest distance and continuing to the first pixel found to satisfy the contrast condition; and
   means for associating distance information with said pixel from said map of distances, said distance information being the visibility distance.

2. A device according to claim 1, in which the means for generating the map of distances comprise another camera suitable for taking a second image of the same landscape from a different angle so as to obtain a stereovision effect, and means for processing the pixels of the two images in order to deduce therefrom information representative of the distance of each pixel in the first image.

3. A device according to claim 1, in which the means for generating the map of distances comprise telemeter means suitable for scanning said landscape in order to associate each pixel of the image with information representative of distance.

4. A device according to claim 1, in which said predetermined value corresponds to contrast lying in the range 2% to 5%.

5. A device according to claim 1, the device being mounted on a vehicle.

* * * * *